United States Patent [19]

Schultz

[11] Patent Number: 5,536,400
[45] Date of Patent: Jul. 16, 1996

[54] APPARATUS FOR PURIFYING FLUIDS WITH UV RADIATION AND OZONE

[75] Inventor: Jeffrey L. Schultz, Hollywood, Fla.

[73] Assignee: Aqua Care Systems, Inc., Hollywood, Fla.

[21] Appl. No.: 274,975

[22] Filed: Jul. 14, 1994

[51] Int. Cl.⁶ .................... C02F 1/32; C02F 1/78
[52] U.S. Cl. .......... 210/192; 210/199; 210/205; 422/186.12; 422/186.3
[58] Field of Search .................. 210/748, 760, 210/192, 199, 205, 218; 422/186.12, 186.3

[56] References Cited

U.S. PATENT DOCUMENTS

| | | |
|---|---|---|
| 4,141,830 | 2/1979 | Last . |
| 4,156,652 | 5/1979 | Wiest . |
| 4,179,616 | 12/1979 | Coviello et al. ............. 422/186.12 |
| 4,214,962 | 7/1980 | Pincon . |
| 4,230,571 | 10/1980 | Dadd . |
| 4,267,455 | 5/1981 | Keller ............................. 210/192 |
| 4,273,660 | 6/1981 | Beitzel . |
| 4,274,970 | 6/1981 | Beitzel . |
| 4,504,445 | 3/1985 | Walz . |
| 4,640,782 | 2/1987 | Burleson ......................... 210/192 |
| 4,694,179 | 9/1987 | Lew et al. . |
| 4,798,669 | 1/1989 | Bachhfer et al. . |
| 4,857,204 | 8/1989 | Joklik . |
| 4,992,169 | 2/1991 | Izumiya . |
| 5,174,904 | 12/1992 | Smith, II ........................ 210/759 |
| 5,256,379 | 10/1993 | De Loach ...................... 210/748 |
| 5,266,215 | 11/1993 | Engelhard . |
| 5,320,749 | 6/1994 | Mullen ............................. 210/199 |
| 5,474,748 | 12/1995 | Szabo ............................. 422/186.3 |

Primary Examiner—Peter A. Hruskoci
Assistant Examiner—Theodore M. Green
Attorney, Agent, or Firm—Malin, Haley, DiMaggio & Crosby

[57] ABSTRACT

A method and apparatus for purifying fluids with ozone and ultraviolet radiation. A housing defining an ozone creation chamber having a plurality of ultraviolet radiation sources disposed circumferentially around the inner surface of the housing is provided. Oxygen containing gas, such as ambient air, is directed to flow within the housing. An effluent conduit of ultraviolet radiation permeable material is disposed coaxially within the housing. A venturi is disposed within the effluent conduit. An ozone gas discharge conduit is connected between the ozone creation chamber and the venturi, such that ozonated gas generated within the ozone creation chamber is sucked into the effluent stream flowing within the effluent conduit, thereby purifying the fluid contained therein. The mixture of ozone and fluid passes out the outlet of the effluent conduit and into either a water supply, or is recirculated back through the apparatus for further processing.

15 Claims, 2 Drawing Sheets

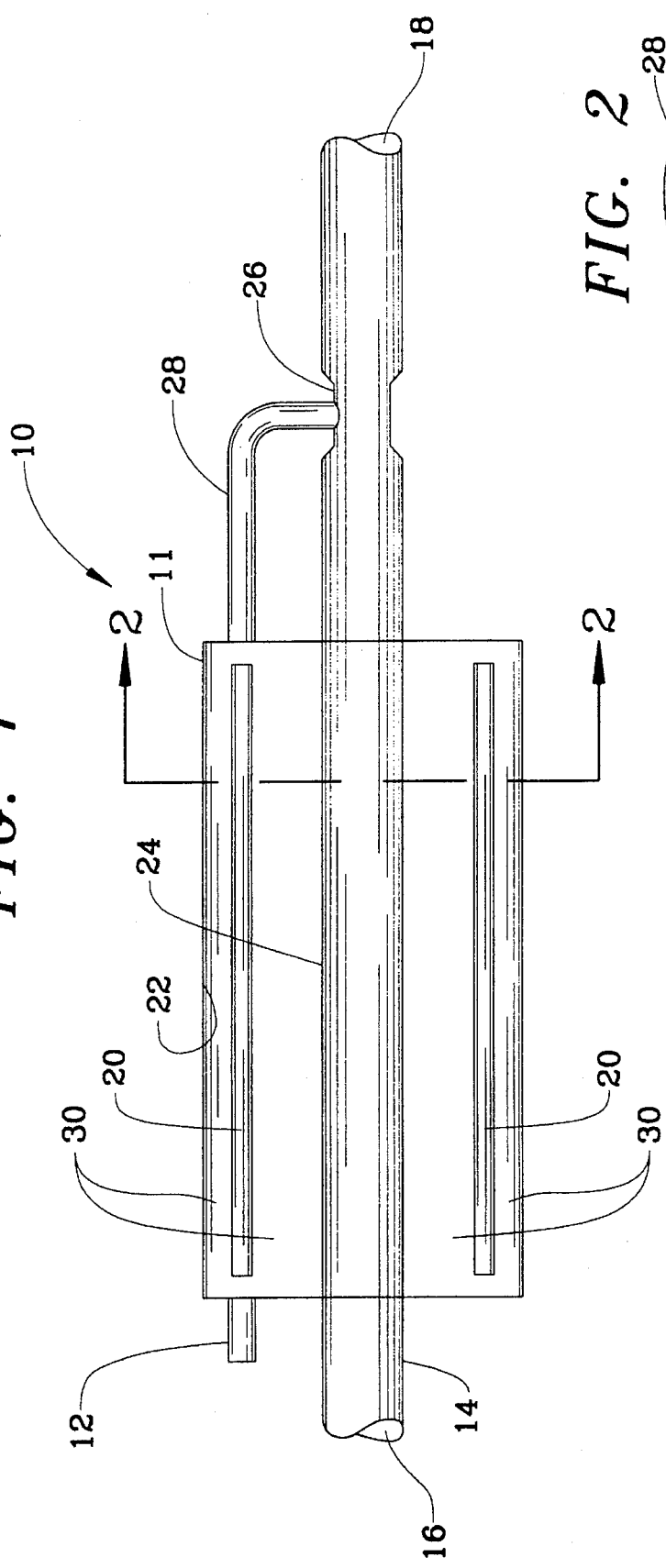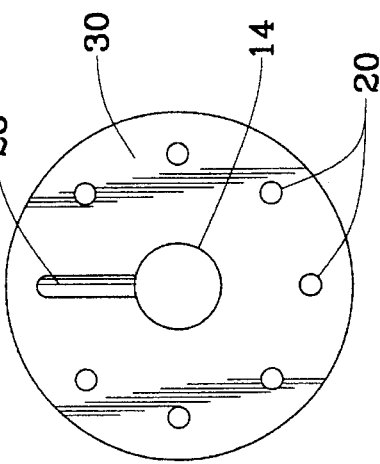

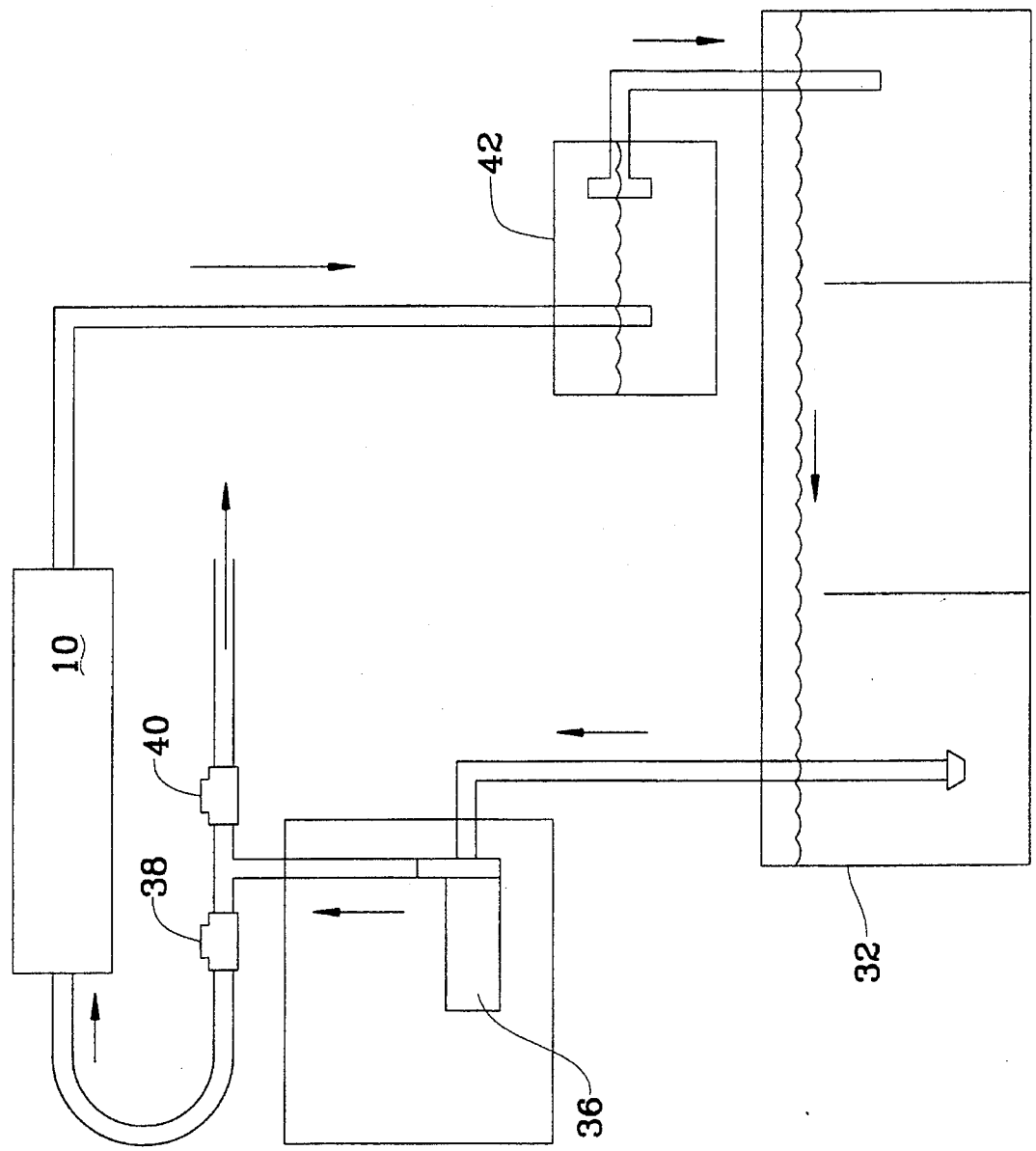

APPARATUS FOR PURIFYING FLUIDS WITH UV RADIATION AND OZONE

BACKGROUND OF THE INVENTION

1. Field of the Invention

The present invention relates to an apparatus and method for purifying fluids, and more particularly, to an apparatus and method for restoring gray water resulting from a cleaning activity such as commercial laundry or commercial car washing, in which the disinfecting properties of both ultraviolet radiation and ozone are combined in order to purify fluids.

2. Description of the Prior Art

There have been a number of attempts to integrate ozone into the process of recovering gray water for reuse in the cleaning cycle. Ozone is a naturally occurring oxygen compound designated as $O_3$. Typically, ozone is generated when oxygen, $O_2$, is exposed to ultraviolet light or an electrical charge which breaks it down to individual oxygen molecules. As it is well known, ozone is an unstable, powerfully bleaching, toxic (only at very elevated concentrations) oxidizing agent used to purify and deodorize air, to sterilize water, and as a bleach. Ozone is also used to control airborne organics, molds, fungus, bacteria, and viruses, by chemically reacting with them.

Prior art devices have provided an apparatus with a radiation chamber in which the disinfecting properties of both ultraviolet radiation and ozone are combined in order to sterilize fluids. Typically, the radiation chamber includes a source of ultraviolet radiation, and a housing having an outer casing spaced from a UV permeable inner casing. The inner casing of the housing is spaced around the source of ultraviolet radiation in such a manner as to form an intermediary channel, and a fluid is conveyed through the space between the casings. The ultraviolet radiation forms ozone in the gas, and has a sterilizing effect in the fluid.

U.S. Pat. No. 4,230,571, issued Oct. 28, 1980 to Dadd, discloses a method and apparatus for the purification of water, in which an ultraviolet radiation source simultaneously produces ozone, irradiates the water, and irradiates the subsequent mixture of water and ozone. The light source in Dadd is disposed centrally of the device.

U.S. Pat. No. 4,214,962, issued Jul. 29, 1980 to Pincon, discloses a structure having circumferentially spaced electromagnetic radiation sources having a wave length less than 200 nanometers, which apparently does not produce ozone.

The foregoing inventions disclose an apparatus for purifying liquid, such as water, in which an ultraviolet light source irradiates air passing through a chamber. However, although various water purifiers are disclosed, none of them show an ozone creation chamber positioned in surrounding relationship about an effluent carrying tube.

SUMMARY OF THE INVENTION

The present invention comprises an apparatus and method for the purification of water in which an ultraviolet radiation source simultaneously produces ozone and irradiates the water. Broadly, the invention comprises a housing defining an ozone creation chamber, a plurality of ultraviolet light sources producing ultraviolet radiation in the 185–254 nanometer wavelength range disposed circumferentially around the inner surface of the housing, thereby generating ultraviolet radiation through a relatively broad spectrum, an effluent conduit for carrying the fluid to be purified disposed coaxially within the housing, an oxygen containing gas directed in a relatively confined path in close proximity to the ultraviolet radiation source so as to produce ozone, and redirecting the ozone containing gas to the water to be purified, such that ozone created within the ozone creation chamber is sucked into the effluent stream flowing within the effluent conduit via a venturi disposed within the effluent conduit.

In accordance with the present invention, ultraviolet radiation in the wave length range of 185 nanometers is absorbed by the air traveling through the ozone creation chamber in close proximity to the ultraviolet light source. This absorption of ultraviolet radiation by oxygen in the moving air produces ozone. The effluent conduit, which is transparent and is preferably quartz crystal, allows the fluid disposed therein to be irradiated with the 185 nanometer ultraviolet radiation.

Simultaneously, ultraviolet radiation in the wave length range of 254 nanometers passes through the moving air, and into the fluid flowing within the effluent conduit. Radiation in this wave length range has a bacteriocidal effect upon bacteria and other viruses present in the flowing liquid.

An ozone gas discharge conduit is connected between a venturi disposed within the effluent conduit and the ozone creation chamber, such that ozonated gas generated within the ozone creation chamber is sucked into the effluent stream flowing within the effluent conduit, thereby sterilizing the fluid contained therein.

In the preferred embodiment of the present invention, a housing defining an ozone creation chamber having a plurality of ultraviolet light sources disposed circumferentially around the inner surface of the housing is provided. An ambient air inlet is connected to the housing for allowing ambient air into the ozone creation chamber. An effluent conduit of ultraviolet radiation permeable material is disposed coaxially within the housing, wherein ambient air is circulated between the housing inner wall and the effluent conduit outer wall. A venturi is disposed within the effluent conduit preferably outside of the ozone creation chamber, although the venturi could be internal of this chamber. An ozone conduit is connected between the ozone creation chamber and the venturi, such that ozonated gas generated within the ozone creation chamber is sucked into the effluent stream flowing within the effluent conduit.

The liquid wastewater to be purified is introduced into the effluent conduit through a water inlet. Simultaneously, an oxygen containing gas, e.g. air, is introduced into the ozone creation chamber through the ambient air inlet, and passes in close proximity to the source of ultraviolet radiation. Ozone is produced and is sucked through the ozone gas discharge conduit and into the venturi and the effluent stream flowing within the effluent conduit. The mixture of ozone and fluid passes out the outlet of the effluent conduit and into either a water supply, or is recirculated back through the apparatus for further processing.

Thus, the present invention provides for an efficient and cost effective apparatus for purifying water. Odors in the water from dissolved hydrogen sulfide gas or other organic sources are eliminated also.

It is an object of this invention to provide an apparatus and method for treating liquid wastewater through the use of ozonated gas produced as a result of ultraviolet light radiation so as to render such water potable by killing bacteria and viruses present within such water.

Another object of this invention is to provide an ozone and UV filter, wherein the ozone creation chamber is positioned in surrounding relationship about an effluent carrying tube.

Still another object of this invention is to provide a water purification apparatus having an outflow free of living microorganisms and particulate matter.

In accordance with these and other objects which will become apparent hereinafter, the instant invention will now be described with particular reference to the accompanying drawings.

BRIEF DESCRIPTION OF THE DRAWINGS

FIG. 1 shows a preferred apparatus for practicing the invention, shown diagrammatically.

FIG. 2 is a cross sectional view taken substantially along line 2—2 of FIG. 1.

FIG. 3 is a block diagram of a water treatment system utilizing the instant invention.

DESCRIPTION OF THE PREFERRED EMBODIMENTS

With reference to the drawings, FIGS. 1 and 2 depict an apparatus for sterilizing fluids with ultraviolet radiation and ozone, generally indicated by the reference numeral 10. The apparatus 10 comprises a housing 11 defining an ozone creation chamber having an inner surface 22, an ambient air inlet conduit 12, an effluent conduit 14 located within the housing having a fluid inlet 16 and a fluid outlet 18, wherein each of the fluid inlet 16 and the fluid outlet 18 are located outside the housing 11, an ultraviolet radiation source 20 such as a tubular ultraviolet lamp located within housing 11 and disposed circumferentially around the inner surface of housing 11, a venturi 26 disposed within effluent conduit 14, preferably outside of the housing 11, and an ozone gas discharge conduit 28 connected between the housing 11 and the venturi 26.

As illustrated in FIGS. 1 and 2, the apparatus 10 has a generally cylindrical shape. The portion of effluent conduit 14 disposed within housing 11 is, in the preferred embodiment, constructed of any suitable ultraviolet radiation permeable material, such as quartz crystal or the like, and has a generally cylindrical shape and is aligned with the central longitudinal axis of housing 11. Effluent conduit 14 passes through both end walls of housing 11 and has an inlet 16 and an outlet 18, each communicating with the exterior of housing 11. At each end of housing 11 is appropriate wiring (not shown) and a plurality of sockets (not shown) for receiving the electrical connections for a plurality of ultraviolet lamps 20.

The embodiment depicted in FIGS. 1 and 2 may be more fully understood by considering the function of the above-described component parts during operation of the apparatus to purify water.

As seen in FIG. 3, water from an external water supply, such as a car wash water reclamation tank 32, is pumped by pump 36 through solenoid 38 and into the apparatus for sterilizing fluids 10. It should be noted that the reclaim water may also be pumped through solenoid 40 to rollover. The reclaim water is introduced into conduit 14 through fluid inlet 16. Simultaneously with the introduction of water from the water supply 32, a power supply (not shown) provides electric current to ultraviolet lamps 20. Thus, ultraviolet radiation emitted from ultraviolet lamp 20 passes through the ultraviolet radiation permeable wall of conduit 16, and into the fluid contained therein. Gas, preferably ambient air, is drawn in through air inlet 12, and into chamber 30 where it is exposed to ultraviolet radiation in the wave length range of 185 nanometers. The absorption by oxygen of ultraviolet radiation in this particular wave length range results in the production of ozone. Furthermore, radiation in the wave length range of 254 nanometers passes through the radiation permeable wall 24 of conduit 14 and into the fluid flowing therein. Ultraviolet radiation in this particular wave length acts as a bactericide upon bacteria and viruses present in the water.

Proximate the outlet of effluent conduit 14 is a venturi 26. An ozone conduit 28 is connected between venturi 26 and the ozone creation chamber 30. Because of the reduction in static fluid pressure at the throat of venturi 26, a sub-atmospheric condition exists. Thus, the fluid flowing through venturi 26 sucks ozonated air from chamber 30 through ozone gas discharge conduit 28 and into effluent conduit 14. Thus, at venturi 26, the water and ozonated air are mixed. The ozone present in the fluid destroys bacteria and viruses and oxidizes undesirable chemical compounds which may be present in the water. The mixture of fluid and ozone exits fluid outlet 18 and is circulated directly into bay sand pit or sand trap 42, or more desirably, directly into reclamation tank 32 where it can be reused, or alternately, the water is recirculated back through the device for further processing.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An apparatus for purifying a fluid, comprising:

a housing defining an ozone creation chamber;

a source of ultraviolet radiation disposed circumferentially around an inner surface of said housing;

an effluent conduit for carrying the fluid to be purified, said effluent conduit being permeable to ultraviolet radiation and being disposed coaxially within said housing;

means for introducing oxygen into said ozone creation chamber, said oxygen in said chamber and oxygen within the fluid being exposed to said source of ultraviolet radiation to produce an ozone-enriched gas; and means for introducing ozone-containing air from said ozone creation chamber into the fluid to be purified.

2. An apparatus for purifying a fluid as recited in claim 1, wherein said means for introducing oxygen comprises an air inlet conduit.

3. An apparatus for purifying a fluid as recited in claim 1, wherein said means for introducing ozone-containing air comprises a venturi disposed within said effluent conduit.

4. An apparatus for purifying a fluid as recited in claim 3, wherein said means for introducing ozone-containing air further comprises an ozone gas discharge conduit connected between said venturi and said ozone creation chamber.

5. An apparatus for purifying a fluid as recited in claim 4, wherein a portion of said effluent conduit extends through at least one end wall of said housing, and further wherein said venturi is disposed within the portion of said effluent conduit that extends through said at least one end wall, such that said venturi is disposed outside of said housing.

6. An apparatus for purifying a fluid as recited in claim 1, wherein said source of ultraviolet radiation is a tubular lamp.

7. An apparatus for purifying a fluid as recited in claim 1, wherein said effluent conduit is constructed of quartz crystal.

8. An apparatus for purifying a fluid, comprising:

a substantially cylindrical housing defining an ozone creation chamber;

a plurality of ultraviolet lamps disposed circumferentially around an inner surface of said housing for producing ultraviolet radiation;

an air inlet conduit connected to said housing for introducing oxygen into said ozone creation chamber, the oxygen being exposed to the ultraviolet radiation to produce an ozone-enriched gas;

a substantially cylindrical effluent conduit for carrying the fluid to be purified, said effluent conduit being permeable to ultraviolet radiation thereby allowing oxygen in said fluid to be converted to ozone-enriched gas, said effluent conduit disposed within said housing, said effluent conduit being aligned with a central longitudinal axis of said housing, a portion of said effluent conduit passing through at least one end wall of said housing;

a venturi disposed within the portion of said effluent conduit that extends through said at least one end wall, such that said venturi is disposed outside of said housing; and an ozone gas discharge conduit connected between said venturi and said ozone creation chamber for introducing ozone-containing air from said ozone creation chamber into the fluid to be purified.

9. An apparatus for purifying a fluid, comprising:

a housing defining an ozone creation chamber;

a source of ultraviolet radiation disposed circumferentially around an inner surface of said housing;

an ultraviolet permeable effluent conduit having a fluid inlet and a fluid outlet, said fluid inlet and said fluid outlet being coaxial, said conduit carrying the fluid to be purified and being disposed coaxially within said housing;

means for introducing oxygen into said ozone creation chamber, said oxygen in said chamber and oxygen within the fluid being exposed to said source of ultraviolet radiation to produce an ozone-enriched gas; and means for introducing ozone-containing air from said ozone creation chamber into the fluid to be purified.

10. An apparatus for purifying a fluid as recited in claim 9, wherein said means for introducing oxygen comprises an air inlet conduit.

11. An apparatus for purifying a fluid as recited in claim 9, wherein said means for introducing ozone-containing air comprises a venturi disposed within said effluent conduit.

12. An apparatus for purifying a fluid as recited in claim 11, wherein said means for introducing ozone-containing air further comprises an ozone gas discharge conduit connected between said venturi and said ozone creation chamber.

13. An apparatus for purifying a fluid as recited in claim 12, wherein a portion of said effluent conduit extends through at least one end wall of said housing, and further wherein said venturi is disposed within the portion of said effluent conduit that extends through said at least one end wall, such that said venturi is disposed outside of said housing.

14. An apparatus for purifying a fluid as recited in claim 9, wherein said source of ultraviolet radiation is a tubular lamp.

15. An apparatus for purifying a fluid as recited in claim 9, wherein said effluent conduit is constructed of quartz crystal.

* * * * *